United States Patent
Drapeau et al.

(10) Patent No.: US 10,631,893 B2
(45) Date of Patent: Apr. 28, 2020

(54) NERVE AND SOFT TISSUE REMOVAL DEVICE

(71) Applicant: Warsaw Orthopedic, Inc., Warsaw, IN (US)

(72) Inventors: Susan J. Drapeau, Collierville, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 752 days.

(21) Appl. No.: 14/796,467

(22) Filed: Jul. 10, 2015

(65) Prior Publication Data
US 2017/0007277 A1 Jan. 12, 2017

(51) Int. Cl.
| | | |
|---|---|---|
| A61B 18/14 | (2006.01) | |
| A61B 17/32 | (2006.01) | |
| A61B 17/3205 | (2006.01) | |
| A61B 17/22 | (2006.01) | |
| A61B 17/30 | (2006.01) | |
| A61B 17/221 | (2006.01) | |
| A61B 17/00 | (2006.01) | |

(52) U.S. Cl.
CPC ........... *A61B 17/32056* (2013.01); *A61B 17/320016* (2013.01); *A61B 18/1482* (2013.01); *A61B 17/22031* (2013.01); *A61B 17/32053* (2013.01); *A61B 2017/00349* (2013.01); *A61B 2017/2215* (2013.01); *A61B 2017/22079* (2013.01); *A61B 2017/306* (2013.01); *A61B 2017/32004* (2013.01); *A61B 2018/141* (2013.01); *A61B 2217/005* (2013.01); *A61B 2218/007* (2013.01)

(58) Field of Classification Search
CPC ...... A61B 17/32056; A61B 17/320016; A61B 18/1482; A61B 2018/141; A61B 17/22031; A61B 17/32053; 2017/00349; A61B 2017/22079; A61B 2017/2215; A61B 2017/306; 2017/32004; A61B 2217/005; A61B 2017/00358; A61B 17/23056
See application file for complete search history.

(56) References Cited

U.S. PATENT DOCUMENTS

| | | | |
|---|---|---|---|
| 5,035,695 A | * | 7/1991 | Weber, Jr. .......... A61B 18/1402 604/35 |
| 5,147,355 A | | 9/1992 | Friedman et al. |
| 5,201,741 A | * | 4/1993 | Dulebohn ........ A61B 17/32056 606/110 |

(Continued)

FOREIGN PATENT DOCUMENTS

| | | | |
|---|---|---|---|
| WO | 2010102310 A2 | 9/2010 | |
| WO | WO2014035862 | * 3/2014 | ............. A61F 9/007 |

*Primary Examiner* — Jaymi E Della
(74) *Attorney, Agent, or Firm* — Sorell, Lenna & Schmidt, LLP

(57) ABSTRACT

Ablation devices useful for removing nerve and soft tissue via a minimally invasive procedure to alleviate pain are provided. The device comprises a cannula having an opening at a distal tip of the cannula, the opening configured for suction of a surgical site, and a movable tissue capture member having a portion disposed within the opening or adjacent to the cannula, the movable tissue capture member configured to capture tissue when moved in a first position. Methods for ablating nerve and/or soft tissue utilizing the ablation devices are also provided.

12 Claims, 7 Drawing Sheets

(56) References Cited

U.S. PATENT DOCUMENTS

| | | | |
|---|---|---|---|
| 5,334,181 A | | 8/1994 | Rubinsky et al. |
| 5,376,094 A | * | 12/1994 | Kline .................... A61B 17/221 |
| | | | 606/110 |
| 5,417,697 A | * | 5/1995 | Wilk ...................... A61B 18/10 |
| | | | 606/113 |
| 5,520,682 A | | 5/1996 | Baust et al. |
| 5,897,487 A | * | 4/1999 | Ouchi .............. A61B 17/12013 |
| | | | 600/127 |
| 5,906,612 A | | 5/1999 | Chinn |
| 6,007,546 A | * | 12/1999 | Snow ..................... A61B 18/10 |
| | | | 606/110 |
| 6,032,675 A | | 3/2000 | Rubinsky |
| 6,071,233 A | * | 6/2000 | Ishikawa .............. A61B 1/0014 |
| | | | 600/104 |
| 6,179,831 B1 | | 1/2001 | Bliweis |
| 6,190,378 B1 | | 2/2001 | Jarvinen |
| 6,210,416 B1 | * | 4/2001 | Chu ................. A61B 17/32056 |
| | | | 606/113 |
| 6,485,422 B1 | | 11/2002 | Mikus et al. |
| 6,517,550 B1 | * | 2/2003 | Konya ................. A61B 17/221 |
| | | | 606/113 |
| 6,579,287 B2 | | 6/2003 | Wittenberger et al. |
| 6,672,095 B1 | | 1/2004 | Luo |
| 6,761,715 B2 | | 7/2004 | Carroll |
| 6,789,545 B2 | | 9/2004 | Littrup et al. |
| 6,796,979 B2 | | 9/2004 | Lentz |
| 6,902,547 B2 | | 6/2005 | Aves et al. |
| 6,926,711 B2 | | 8/2005 | Lentz et al. |
| 7,381,208 B2 | | 6/2008 | Van Der Walt et al. |
| 7,510,554 B2 | | 3/2009 | Duong et al. |
| 7,625,368 B2 | | 12/2009 | Schechter et al. |
| 7,641,679 B2 | | 1/2010 | Joye et al. |
| 7,846,154 B2 | | 12/2010 | Bliweis et al. |
| 7,938,822 B1 | | 5/2011 | Berzak et al. |
| 7,967,814 B2 | | 6/2011 | Levin |
| 7,967,815 B1 | | 6/2011 | Berzak et al. |
| 8,083,733 B2 | | 12/2011 | Toubia et al. |
| 8,162,812 B2 | | 4/2012 | Shai et al. |
| 2002/0068964 A1 | | 6/2002 | Dobak |
| 2004/0049177 A1 | | 3/2004 | Zvuloni et al. |
| 2005/0177215 A1 | | 8/2005 | Rosenberg |
| 2005/0240239 A1 | | 10/2005 | Boveja et al. |
| 2007/0156125 A1 | | 7/2007 | Delonzor |
| 2007/0191732 A1 | | 8/2007 | Voegele |
| 2008/0306475 A1 | | 12/2008 | Lentz et al. |
| 2009/0036823 A1 | | 2/2009 | Lepivert |
| 2009/0036899 A1 | * | 2/2009 | Carlton ............ A61B 17/32056 |
| | | | 606/113 |
| 2009/0192505 A1 | | 7/2009 | Askew et al. |
| 2009/0299357 A1 | | 12/2009 | Zhou |
| 2010/0168739 A1 | | 7/2010 | Wu et al. |
| 2010/0179527 A1 | | 7/2010 | Watson et al. |
| 2010/0292764 A1 | | 11/2010 | Soomro et al. |
| 2011/0270238 A1 | | 11/2011 | Rizq et al. |
| 2011/0313411 A1 | | 12/2011 | Anderson et al. |
| 2012/0046531 A1 | | 2/2012 | Hua |
| 2012/0065630 A1 | | 3/2012 | Berzak et al. |
| 2012/0089047 A1 | | 4/2012 | Ryba et al. |
| 2012/0109116 A1 | | 5/2012 | Asconeguy et al. |
| 2012/0253336 A1 | | 10/2012 | Littrup et al. |
| 2013/0172828 A1 | * | 7/2013 | Kappel ............ A61B 17/00234 |
| | | | 604/272 |

\* cited by examiner

NERVE AND SOFT TISSUE REMOVAL DEVICE

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's wellbeing, require extended periods of fasting prior to treatment, and are often accompanied by undesirable after effects such as nausea.

One alternative approach that is commonly used for providing pain relief is ablation in which nerves and/or soft tissue is removed and/or destroyed. Two approaches to removing tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which leads to coagulation necrosis. Because ion agitation, and thus tissue heating, is greatest in areas of highest current density (e.g., closest to the active electrode tip), necrosis is limited to a relatively small volume of tissue surrounding the RF electrode.

A form of cold ablation is cryoablation. During cryoablation, tissue is frozen or rapid freeze/thaw cycles are inflicted upon the tissue. There are many advantages to using cryoablation instead of radiofrequency ablation. For example, cryoablation is safer especially near critical vasculature and there is less risk of post-procedure neuritis or neuromas following neuroablation for the treatment of pain. Cryoablation allows treatment mapping pre and post procedure where areas of tissue can be mapped by limited, reversible and/or freezing. Cryoablation can be monitored and visualized on ultrasonography, CT and MRI. Moreover, because nerve cooling is anesthetic, cryoablation is a less painful procedure than thermal ablation techniques.

Other ways of removing soft tissue and nerves utilize cutting instruments like a scalpel or cutting blade. However, when dealing with soft tissue and nerve areas particularly in a delicate area, such as for example, the spinal column, cutting, retraction and removal of tissue can be complicated particularly when multiple entries are required to repair the surgical site. There is often unwanted collateral damage to soft tissue and nerve areas. For example, hypertrophic ligamentum flavum is a prevalent soft tissue disorder that causes pain in patients and is associated with spinal stenosis. This disorder is often treated by decompression of the spine, which often times requires multiple entries into the spine to remove and cut the surrounding tissue. This is not only painful to the patient, but also can lead to complications and prolong the surgical and recovery times.

Accordingly, there is a need for devices and methods that provide efficient removal of nerve and/or soft tissue while reducing or limiting unwanted damage to tissue surrounding the surgical site. There is also a need for devices and methods that allow capture, cutting and removal of soft tissue and nerve areas at or near a surgical site.

SUMMARY

Tissue removal devices and methods are provided that deliver improved tissue resection with minimal unwanted destruction to adjacent nerve and/or soft tissue. The tissue removal devices and methods provided allow the device to be easily positioned in an optimal location.

The disclosed devices and methods can be used in a microinvasive surgical procedure to minimize stress to the patient's body. Since the procedure is microinvasive, it allows for earlier timing in the continuum of patient care. Using the disclosed tissue removal device and methods for microdiscectomies or intra-discal procedures can reduce the invasiveness of these procedures, resulting in more efficient surgical and patient recovery times.

In one embodiment, there is a medical device for a minimally invasive surgical procedure comprising a cannula having an opening at a distal tip of the cannula, the opening configured for suction of a surgical site, and a movable tissue capture member having a portion disposed within the opening or adjacent to the cannula, the movable tissue capture member configured to capture tissue when moved in a first position.

In another embodiment, there is a medical device for a minimally invasive surgical procedure comprising a cannula having an opening at a distal tip of the cannula, the opening configured for suction of a surgical site, and a movable tissue capture member having a portion disposed within the opening of the cannula, the movable tissue capture member having a cutting surface and configured to capture tissue when moved in a first position.

In one exemplary embodiment, there is a method for a minimally invasive surgical procedure comprising inserting a medical device for a minimally invasive surgical procedure at a surgical site, the medical device comprising a cannula having an opening at a distal tip of the cannula, the opening configured for suction of the surgical site, and a movable tissue capture member having a portion disposed within the opening or adjacent to the cannula, the movable tissue capture member configured to capture tissue when moved in a first position; and applying suction in the opening of the cannula to remove the captured tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
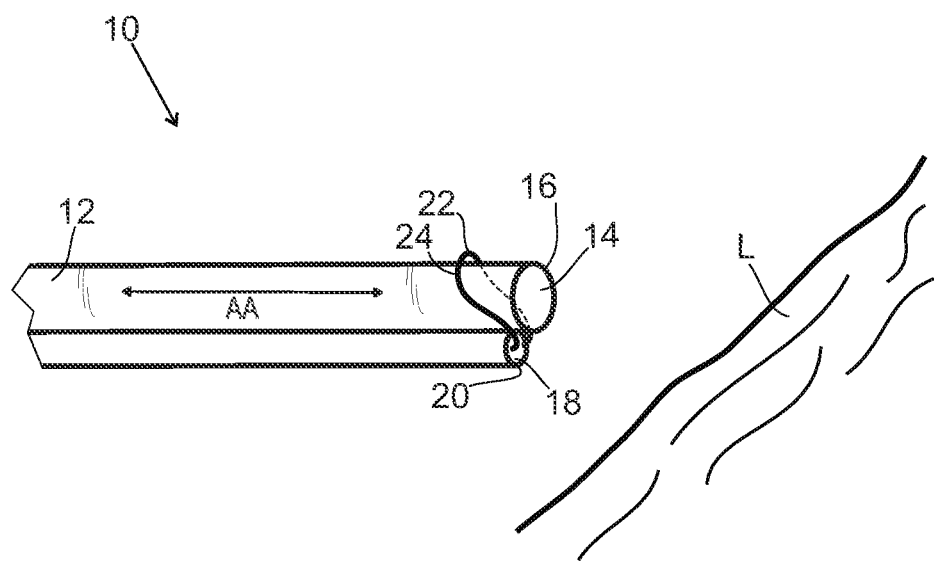
FIG. 1 illustrates a perspective view of a tissue removal device in proximity with tissue shown as tissue L, such as a ligamentum flavum. The tissue removal device includes a loop having a cutting surface that rests on an outer surface of a cannula.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for efficient destruction and/or removing of a material or substance such as nerve and soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Definitions

As used in the specification and including the appended claims, the singular forms "a", "an", and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the cannula portion of the device that is described herein, and "rearward" or "proximal" (and forms thereof) means rearward or away from the direction of the forward, distal end of the cannula portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Tissue Removal Device

At times, soft tissue may impinge on nerves and the spinal cord. In some cases, this leads to neurogenic claudication, which is a source of severe discomfort for a patient. Other soft tissues can cause pain to a patient as well, such as a frayed meniscus. The presently disclosed device and associated methods are capable of removing soft tissue through a minimally invasive surgical procedure. A cutting edge may be used in tandem with a suction tube that grasps, stabilizes, cuts and/or captures the soft tissue. The tissue is retracted from the nerves or spinal cord to allow safe removal of the tissue while minimizing damage to adjacent surrounding tissue. The device may further utilize suction to facilitate removal of the soft tissue without having to retract the device from the patient.

The present disclosure includes tissue removal device 10 capable of efficiently removing selected portions of tissue, such as, for example tissue L, such as a ligamentum flavum to reduce unwanted damaging and/or destroying of adjacent nerve or soft tissue. As illustrated in FIGS. 1-4, the present tissue removal device 10 comprises a tube, such as, for example, cannula 12. Cannula 12 may include a flexible character to facilitate manipulation during a surgical procedure. However, in other embodiments, cannula 12 may be rigidly formed. The dimensions of the device, among other things, will depend on the site from which tissue must be removed. For example, the width of the epidural space is only about 3-5 mm for the thoracic region and about 5-7 mm for the lumbar region. Thus, the device, in various embodiments, can be designed for these specific areas and have cutting lines, cannulas, and/or lumens in these size ranges or smaller. Alternatively, the device can be larger, such as for example, 1 cm or larger.

Some examples of lengths of cannula 12, may include, but are not limited to, from about 50 to 150 mm in length, for example, about 65 mm for epidural pediatric use, about 85 mm for a standard adult and about 110 mm for an obese adult patient. The thickness of cannula 12 will depend on the site from which tissue is to be removed and/or the particular embodiment of the device. In some embodiments, the thickness of cannula 12 is about 20 gauge. In some embodiments, cannula 12 can be about 18 to about 22 gauge. In various embodiments, the thickness includes, but is not limited to, from about 0.05 to about 1.655 mm. In some embodiments cannula 12 can be increasing and or decreasing in thickness throughout the length of cannula 12. In some embodiments, cannula 12 may be tapered and/or angled. Cannula 12 may be the widest or smallest diameter or a diameter in between for insertion into a human or animal body. In some embodiments, the widest diameter is typically about 14 gauge, while the smallest diameter is about 26 gauge.

Suitable materials that cannula 12 or lumen 18 can be made from are, for example, polyurethane, polyurea, polyether(amide), PEBA, thermoplastic elastomeric olefin, copolyester, and styrenic thermoplastic elastomer, steel, aluminum, stainless steel, titanium, nitinol, tungsten, molybdenum, metal alloys with high non-ferrous metal content and a low relative proportion of iron, carbon fiber, glass fiber, plastics, ceramics or a combination thereof.

Cannula 12 extends along a longitudinal axis AA and includes an opening 14. In some embodiments, opening 14 extends through the length of cannula 12 and terminates at tip 16. Tip 16 is at the distal end of cannula 12, and is configured to contact tissue, such as, for example, tissue L. Tip 16 defines an opening that is in communication with opening 14. The cannula can provide the suction for aid in grasping the tissue and for tissue that is cut to be removed. In some embodiments, the cannula is configured to be coupled to a suction device (e.g., vacuum) to provide the suction to grasp and/or remove tissue.

Figure 2:
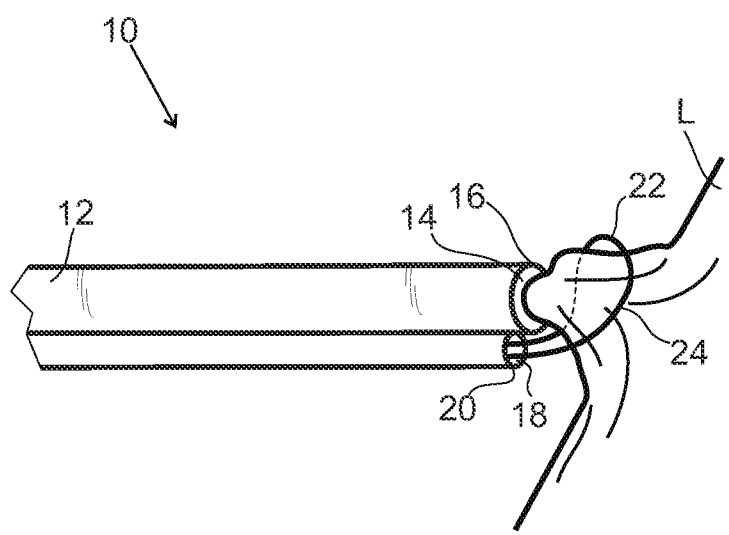
FIG. 2 illustrates a perspective view of a tissue removal device as in FIG. 1 in which the cannula applies a suction force through a lumen to grasp and secure tissue L. Once tissue L is secured by the suction, the loop is retracted to sever the secured portion of tissue L, the device allows capture and cutting of the tissue.
Figure 3:
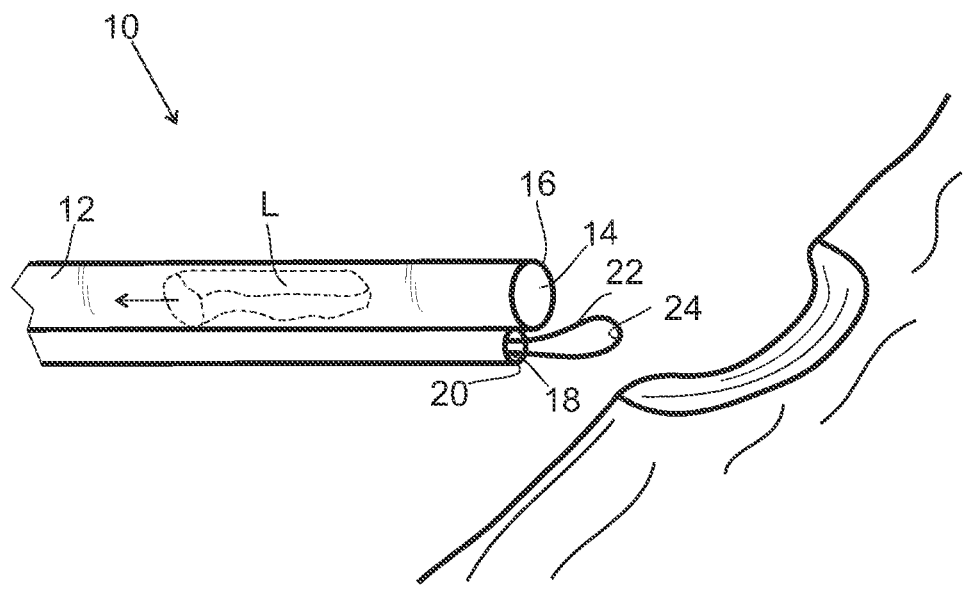
FIG. 3 illustrates a perspective view of a tissue removal device as in FIG. 1 in which the cannula applies a suction force through a lumen to remove the cut portion of tissue L.
Figure 4A:
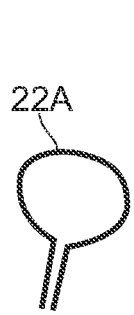
FIGS. 4A, 4B, 4C, 4D, and 4E illustrate side views of a variety of predetermined cutting line shapes which may be used with the tissue removal device of FIG. 1 according to the needs of a medical practitioner.
Figure 4B:
Figure 4C:
Figure 4D:
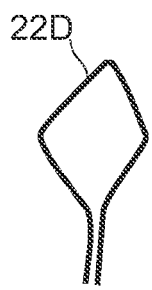
Figure 4E:
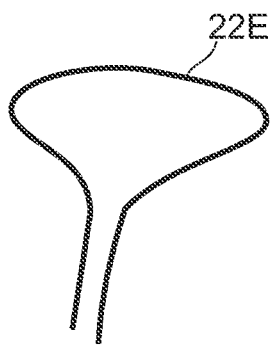

In some embodiments, cannula 12 can have one or more lumens. In one embodiment, as shown in FIGS. 1-3, cannula 12 includes a lumen 18 having a distal opening 20. In various embodiments, the lumens of cannula 12 may have alternate cross-sectional configurations. For example, the lumens may have a cross-sectional shape of oval, oblong, triangular, rectangular, square, polygonal, irregular, uniform, non-uniform, variable, tubular and/or tapered. Lumen 18 runs adjacent to and parallel with opening 14. However, lumen 18 may run adjacent with opening 14 such that lumens 14, 18 are coaxially aligned with one another.

In some embodiments, cannula 12 and lumen 18 are extend straight along a longitudinal axis between proximal and distal ends. In alternative embodiments, cannula 12 and lumen 18 includes a curved portion. For example, cannula 12 and lumen 18 may have a curved portion that forms an angle between the proximal and distal ends. In some embodiments, the distal tip of cannula 12 and lumen 18 are curved. In some embodiments, a portion of cannula 12 and lumen 18 is deflectable to allow a medical practitioner to bend cannula 12 in a desired configuration to suit a medical procedure.

As shown, lumen 18 includes an inner diameter that is less than that of opening 14. However, in other embodiments, lumen 18 includes an inner diameter that is greater than or equal to that of opening 14. Opening 14 is sized accordingly to provide suction to a surgical site and to facilitate removal of tissue during a surgical procedure. In some embodiments, opening 14 includes a diameter between about 1 mm to about 7 mm, 2 mm to about 6 mm, or 3 mm to about 5 mm. Lumen 18 is sized to facilitate translational movement of a flexible cutting line 22, as discussed herein. Thus, in some embodiments, lumen 18 includes a diameter of between about 0.1 mm to about 2 mm, 0.1 to about 1 mm, or 0.3 mm to 0.5 mm. In some embodiments, the cannula can have a larger diameter relative to the lumen or they can have both the same diameter. The capture member shown as flexible cutting line 22 can be disposed within the lumen and a portion deployed outside the lumen and contacting the cannula.

Cannula 12 is configured to provide suction at a surgical site. The suction eliminates the need to repeatedly retract device 10 from a surgical site during a surgical procedure. The suction is applied with sufficient force to pull a membrane or tissue, such as, for example, tissue L toward device 10. Tip 16 is configured to receive a portions of tissue L and to retain tissue L once a vacuum is created in opening 14. Thus, in various embodiments, tip 16 may be a blunt surface so as to prevent unintentional damage to tissue L. In other embodiments, tip 16 is pointed to allow for easy pushing through tissues to reach a surgical site. The openings may be shaped as a regular or irregular polygon including arcuate, round, square, oblong, kidney shaped, crescent, or beveled shaped. In some embodiments, therapeutic agents can be delivered to the surgical site via the openings. In various embodiments, the tip of the cannula can be round or tapered. In some embodiments, the cannula and/or lumen can be curved. In some embodiments, the tip of the cannula and/or lumen can be curved at an angle from about 5 degrees to about 20 degrees or from about 10 degrees to about 30 degrees.

In various embodiments, device 10 can be operatively connected to a vacuum at a distal end (not shown) for providing suction to ablated nerve and/or tissue. The vacuum may be used to transmit vacuum from a vacuum source (not shown) to a receiving aperture (not shown) connected to device 10. Any suitable aspirator, cylindrical or otherwise, or other mechanism that creates vacuum upon the movement of an actuating member thereof, may be utilized as a vacuum source. The vacuum can be in communication with the tips of device 10 for providing suction to remove ablated nerve and/or soft tissue.

Cannula 12 includes a flexible cutting line 22. In various embodiments, flexible cutting line 22 may comprise a suture or wire. Flexible cutting line 22 may be flexible or have a shape memory characteristic. For example, as shown in FIG. 4, the flexible cutting line may comprise a variety of shapes. A medical practitioner may utilize a circular cutting line 22A, an elliptical cutting line 22B, a rectangular cutting line 22C, a diamond cutting line 22D, or an irregularly shaped cutting line 22E. In some embodiments, cutting lines 22A-E are formed from a shape memory material, such as nitinol. The cutting line can have a sharp portion designed for cutting and a blunt portion that can be coated to prevent unwanted tissue damage. In some embodiments, the cutting line can be conductive to conduct radiofrequency (RF) energy through it to aid in cutting tissue.

In one embodiment, flexible cutting line 22 is disposed within lumen 18. The filament is about 0.25 mm in diameter. In some embodiments, the suture or wire of flexible cutting line 22 is about 0.01 mm to 0.5 mm or about 1.0 mm to about 7.0 mm in diameter. Flexible cutting line 22 includes two ends terminating from the proximal end of the device 10 (not shown) such that a cutting loop 24 is formed and extends from tip 16. Cutting loop 24 defines an interior gap shape configured to cut and capture tissue. In one embodiment, flexible cutting line 22 is movable between a first configuration, such as for example, an undeployed position, and a second configuration, such as, for example, a cutting position. While in the undeployed position, flexible cutting line 22 is wrapped around an outer surface of cannula 12 at a point proximal to tip 16 so as to keep cutting loop 24 out of contact with tissue L. While in the cutting position, flexible cutting line 22 is positioned distally to tip 16 adjacent to tissue secured in opening 14. To cut tissue, flexible cutting line 22 is moved axially along a proximal direction through lumen 18 to reduce the size of cutting loop 24. As cutting loop 24 becomes smaller, flexible cutting line 22 captures tissue L adjacent tip 16 to cut a portion of tissue L and the tissue is removed through suction from the cannula, as discussed herein. The cutting loop 24 can capture tissue as shown in FIG. 2.

In one embodiment, cutting loop 24 is deformable so that the shape of the interior gap conforms to the shape of the tissue to be cut. In other embodiments, cutting loop 24 includes a shape memory characteristic, and is partially deformable to conform to the shape of tissue but biased to a predefined shape.

Cutting loop 24 includes a cutting surface configured to cut or sever selected portions of tissue L from a surgical site when brought into contact with tissue L. Cutting loop 24 is energized to cut through tissue. In one embodiment, cutting loop 24 includes a serrated portion which is oscillated to cut through tissue. In other embodiments, cutting loop 24 includes a sharpened edge to cut through tissue. In various embodiments, an energy source is provided in communication with an edge of cutting loop 24 through a wire connected at the proximal end of flexible cutting line 22 (not shown). The energy source may provide energy in the form of electrical, radiation, light, RF, ultrasound, cryotherapy, thermal, microwave or hydromechanical energy.

In various embodiments, cannula 12 and/or lumen 18 comprises an insulated material such as, for example, a heat resistant plastic. Examples of such heat resistant plastics include, but are not limited to PMMA, PET, PEEK, PLA, PLGA, PVC and/or HDPE. In various embodiments, cannula 12 comprises other insulated materials including, but not limited to glass, ceramic, porcelain, composite polymers and/or rubber. Examples of such rubbers include, but are not limited to silicone, fluorosilicone, isobutylene-isoprene copolymer, chlorobutyl, fluroelastomers, and/or polychloroprene. In some embodiments, flexible cutting line 22 is disposed within lumen 18 of cannula 12. In various embodiments, cutting loop 24 of flexible cutting line 22 is configured for axial movement through lumen 18. In various embodiments, cutting loop 24 may comprise of copper, silver, gold, aluminum, brass, platinum, molybdenum and/or tungsten. In some embodiments, cutting loop 24 includes an electrical lead that is approximately 1-2 cm in length and is the same diameter as the cannula.

In one embodiment, the present tissue removal device 10 comprises a cannula 112 similar to cannula 12, as shown in FIGS. 5-8. Cannula 112 may include a flexible or semi-flexible character to facilitate manipulation during a surgical procedure. However, in other embodiments, cannula 112 may be rigidly formed to facilitate implantation into a surgical site. The dimensions of the device, among other things, will depend on the site from which tissue must be removed. For example, the width of the epidural space is only about 3-5 mm for the thoracic region and about 5-7 mm for the lumbar region. Thus, the device, in various embodiments, can be designed for these specific areas.

Cannula 112 extends along a longitudinal axis and includes an opening 114. In some embodiments, opening 114 extends through the length of cannula 112 and terminates at tip 116. Tip 116 is at the distal end of cannula 112, and is configured to contact tissue L, such as, for example, a ligamentum flavum. Tip 116 defines an opening that is in communication with opening 114. In some embodiments, cannula 112 can have one or more openings or lumens. In various embodiments, opening 114 of cannula 112 may have alternate cross-sectional configurations. For example, opening 114 may have a cross-sectional shape of oval, oblong, triangular, rectangular, square, polygonal, irregular, uniform, non-uniform, variable, tubular and/or tapered.

Opening 114 is sized accordingly to provide suction to a surgical site and to facilitate removal of tissue during a surgical procedure. In some embodiments, opening 114 includes a diameter between about 1 mm to about 7 mm, 2 mm to about 6 mm, or 3 mm to about 5 mm.

In some embodiments, device 10 includes a cutting line 122. In various embodiments, cutting line 122 may comprise a suture or wire attached at a distal end of a rigid longitudinal member, such as, for example, a stem 118. Stem 118 may be flexible or semi-flexible. In some embodiments, the suture or wire of cutting line 122 is about 0.25 mm in diameter. In some embodiments, the cutting line 122 is about 0.01 mm to 0.5 mm or about 1.0 mm to about 7.0 mm in diameter. Cutting line 122 includes a cutting loop 124 formed at the distal end of stem 118. Cutting loop 124 defines an interior gap shape configured to cut and capture tissue. In one embodiment, cutting loop 124 is deformable so that the shape of the interior gap conforms to the shape of the tissue to be cut. In other embodiments, cutting loop 124 includes a shape memory characteristic, and is partially deformable to conform to the shape of tissue but biased to a predefined shape. The cutting loop is an example of a movable tissue capture member.

In some embodiments, the cannula 112 comprises a channel 117 that is configured for the stem 118 of the cutting loop 124 to slide longitudinally relative to the cannula about its exterior to ease capture of tissue. The channel 117 can be continuous with the exterior of the cannula 112 and can allow smooth and steady movement of the stem 118. In some embodiments, the tip of the cannula can be curved at an angle from about 5 degrees to about 20 degrees or from about 10 degrees to about 30 degrees.

Figure 5:
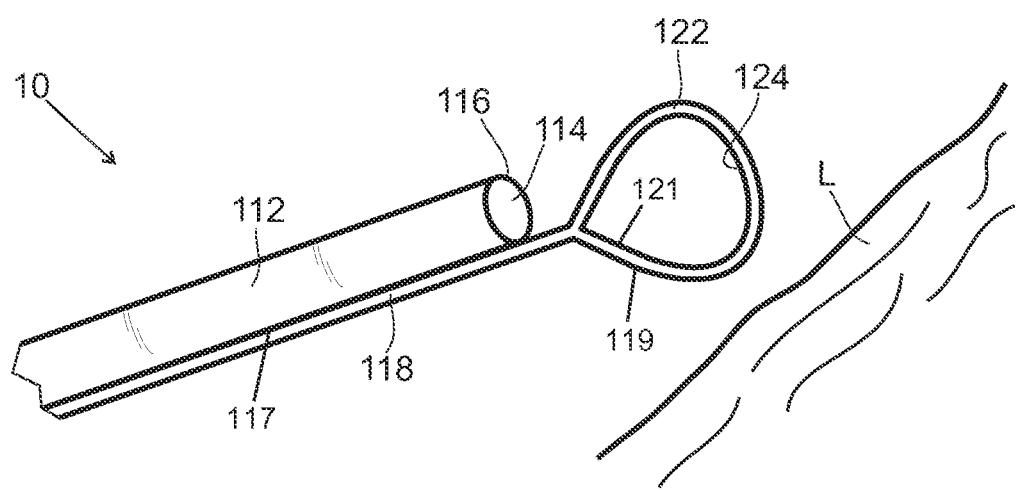
FIG. 5 illustrates a perspective view of a tissue removal device in proximity with tissue shown as tissue L, such as a ligamentum flavum. The tissue removal device includes a loop having a cutting surface that is advanced via a channel along an outer surface of a cannula.
Figure 6:
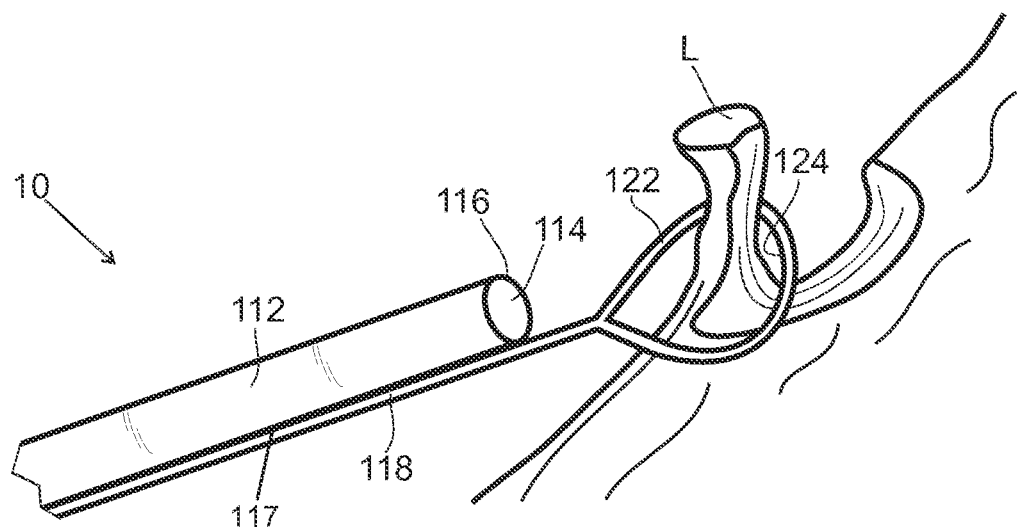
FIG. 6 illustrates a perspective view of a tissue removal device as in FIG. 5 in which the cannula applies a suction force through a lumen to pull tissue L. Once tissue L is pulled by the suction, the loop is positioned and moved to cut a portion of tissue L and the suction can remove the tissue.
Figure 7:
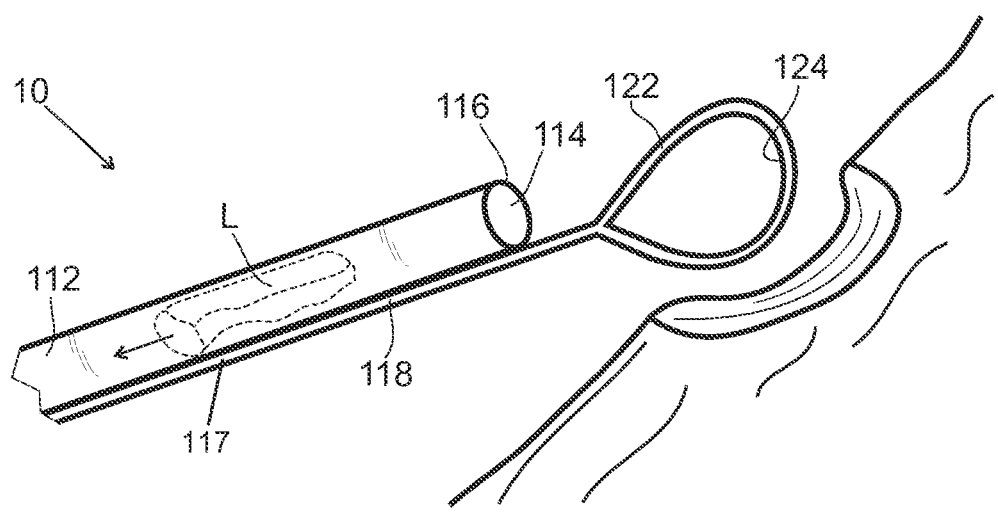
FIG. 7 illustrates a perspective view of a tissue removal device as in FIG. 5 in which the cannula applies a suction force through a lumen to remove the cut portion of tissue L.

In some embodiments, as shown in FIG. 5, the cutting loop 124 can comprise a sharp surface 121 for cutting tissue, while having a blunt surface 119 opposing the sharp surface 121. This blunt surface 119 prevents unwanted tissue damage and can be coated with a polymer to provide a smooth surface. In some embodiments, the tip of the cannula 112 can be curved at an angle from about 5 degrees to about 20 degrees or from about 10 degrees to about 30 degrees.

Figures 8A, 8B, 8C, 8D:
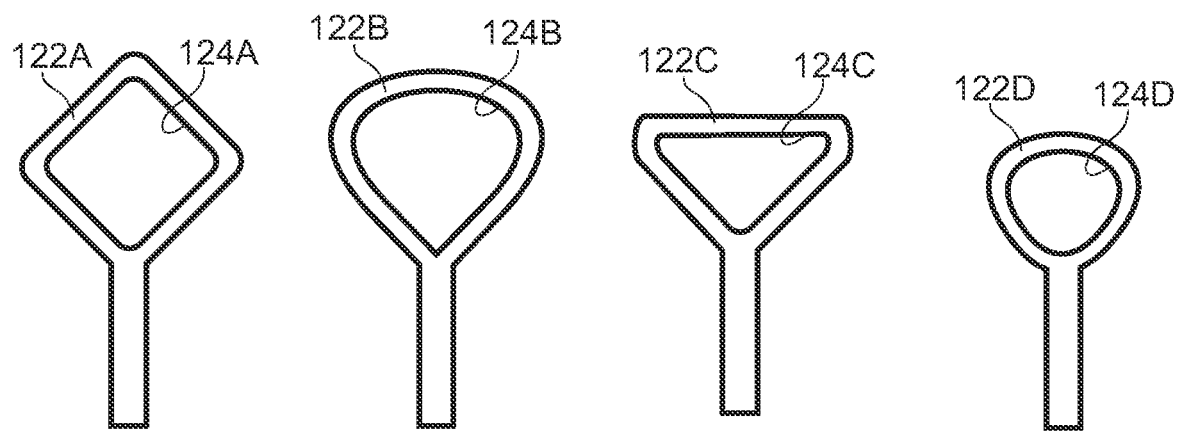
FIGS. 8A, 8B, 8C, and 8D illustrate a side view of a variety of predetermined loop shapes which may be used with the tissue removal device of FIG. 5 according to the needs of a medical practitioner.

Cutting line may be flexible or include a shape memory characteristic. For example, as shown in FIG. 8, the flexible cutting line may comprise a variety of shapes. A medical practitioner may utilize a polygonal cutting line 122A defining an angular cutting loop 124A, a tear shaped cutting line 122B defining a rounded cutting loop 124B, a triangular cutting line 122C defining a straight cutting loop 124C, or a circular shaped cutting line 122D defining a circular cutting surface 124D. In some embodiments, cutting lines 122A-D are formed from a shape memory material, such as nitinol.

Cutting loop 124 includes a cutting surface configured to capture and cut selected portions of tissue L from a surgical site when brought into contact with tissue L. Cutting loop 124 is energized to cut through tissue. In one embodiment, cutting loop 124 includes a serrated portion which is oscillated to cut through tissue. In other embodiments, cutting loop 124 includes a sharpened edge to cut through tissue. In various embodiments, an energy source is provided in communication with an edge of cutting loop 124 through a wire connected at the proximal end of flexible cutting line 122 (not shown). The energy source may provide energy in the form of electrical, radiation, light, radiofrequency, ultrasound, cryotherapy, thermal, microwave or hydromechanical energy.

Figure 9:
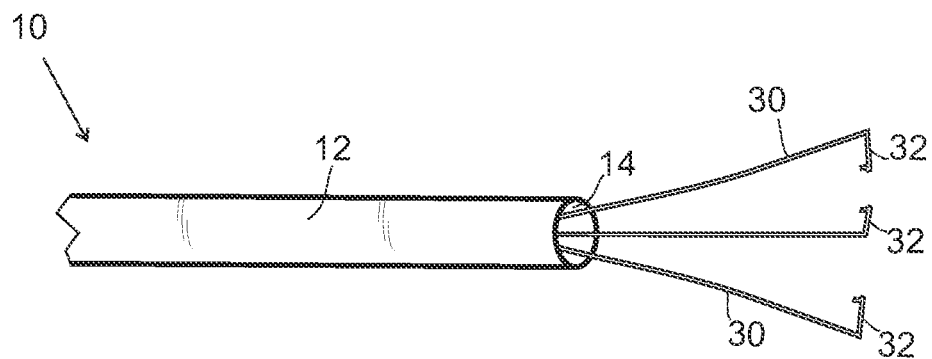
FIG. 9 illustrates a perspective view of a tissue removal device having a plurality of grasping members extending from a lumen of the tissue removal device. As shown, the grasping members are in a first position or a deployed configuration.
Figure 10:
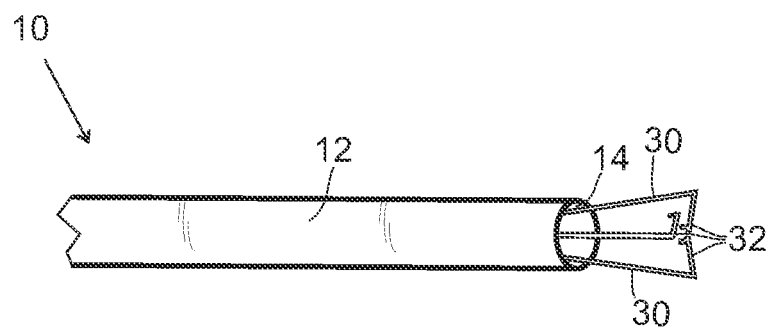
FIG. 10 illustrates a perspective view of a tissue removal device having a plurality of grasping members extending from a lumen of the tissue removal device. As shown, the grasping members are in an undeployed position or a retracted configuration.

In some embodiments, as shown in FIGS. 9 and 10, cannula 12 includes one or more grasping members 30. These are also tissue capture members. Grasping members 30 are disposed in opening 14 and are configured to grasp tissue, such as a ligamentum flavum, as discussed herein. Grasping members 30 include grasping fingers 32 at a distal end of members 30. In some embodiments, grasping fingers 32 comprise sharpened barbs oriented at an angle relative to grasping members 30. In one embodiment, grasping fingers 32 are oriented at a right angle relative to grasping members 30. Grasping members 30 are manipulable to be brought into contact with and grasp tissue. In various embodiments, grasping fingers 32 include sharpened ends, hooks or multiple barbs to secure tissue. The grasping members 30 may have discrete regions that are sharp and discrete regions that are blunt depending on the tissue area and surgical site to the cut. These grasping members are slidable along the longitudinal axis of the cannula and can be slid out of the opening 14 to grasp and capture as well as cut tissue.

Grasping members 30 are configured to fit into opening 14, but prevent obstruction of the suction capability of cannula 12. In one embodiment, grasping members 30 are about 1.0 mm in diameter. In some embodiments, the diameter of grasping members 30 are about 0.01 mm to 5.0 mm or about 0.7 mm to about 1.3 mm. In some embodiments, the plurality of grasping members 30 include the same diameter, and in other embodiments the diameter of grasping members 30 is varied according to the needs of a surgical procedure. For example, one grasping member 30 may be thicker than the others to provide a preliminary grip on tissue, while one or more other grasping members 30 may be thinner to be more easily manipulable to stretch or grasp portions of tissue to be cut. Such a configuration allows a medical practitioner to cut tissue to a predetermined specification in one slice. Furthermore, grasping members 30 may be flexible, semi-flexible, or flexible along certain predetermined portions to facilitate grasping of tissue. One or more grasping members may be rigid to facilitate secure grasping.

In various embodiments, grasping members are movable between a first configuration, such as, for example, a retracted state, and a second configuration, such as, for example, a deployed state. As shown in FIG. 9, when in the deployed state grasping members 30 extend distally from tip 16 to contact and engage tissue. As shown in FIG. 10, when in the retracted state grasping members 30 are close to tip 16 to facilitate implantation to a surgical site. Cannula 12 is inserted into a surgical site while the grasping members 30 are in the retracted state, and once in position the grasping members 30 are extended to the deployed position to contact tissue. Once positioned, grasping members 30 are manipulated such that grasping fingers 32 engage tissue, and grasping members 30 are brought back to the retracted position. In some embodiments, grasping members 30 are in communication with an actuator (not shown) to move between the deployed and retracted states. In some embodiments, the first position can be where the capture member captures tissue and the second position can be where the capture member cuts tissue.

Figure 11:
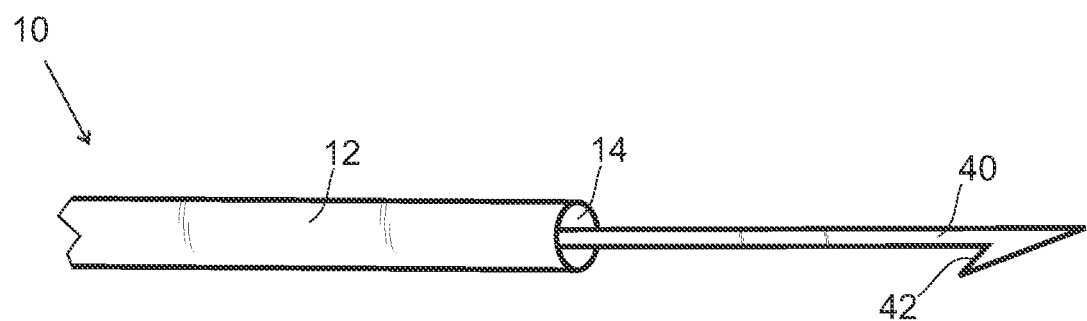
FIG. 11 illustrates a perspective view of a tissue removal device having a hook shaped cutting edge extending from a lumen of the tissue removal device in a first position. The hook shaped cutting edge as shown may be extended through the lumen, positioned at a portion of tissue to be cut, and retracted to cut the tissue.

In some embodiments, cannula 12 is used together with a hook 40, as shown in FIG. 11. Hook 40 is axially movable through opening 14 of cannula 12 to cut and capture tissue. Hook 40 includes a distal barb having a cutting surface 42 positioned on the inside of the barb. Hook 40 defines a distal point to facilitate advancement through tissue to reach a surgical site. Hook 40 is advanced axially through opening 14 to reach a portion of tissue. The tissue may be secured at a predetermined portion by suction through opening 14 or by grasping members such as those shown in 30 of FIG. 10. Hook 40 is advanced to the secured portion of tissue and cutting surface 42 cuts and captures tissue. In some embodiments, the tip of the cannula can be curved at an angle from about 5 degrees to about 20 degrees or from about 10 degrees to about 30 degrees.

Figure 12:
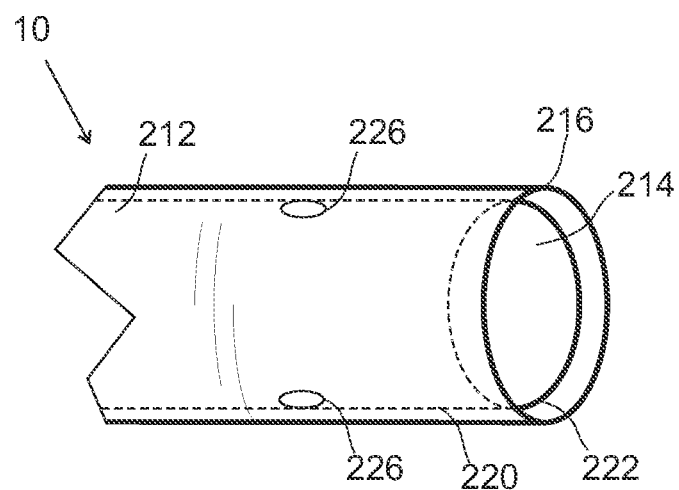
FIG. 12 illustrates a perspective view of a tissue removal device having a cutting surface that positioned within and in a coaxial relationship with the lumen of the device.
Figure 13:
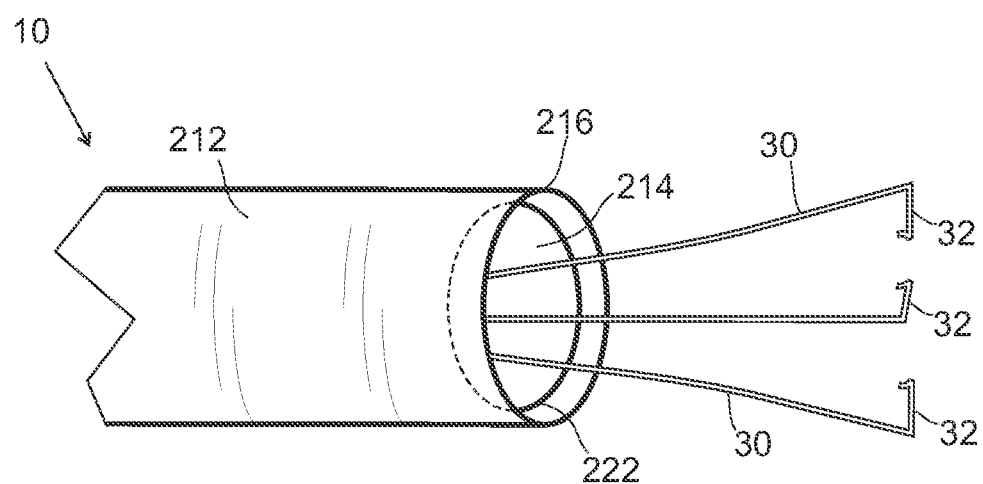
FIG. 13 illustrates a perspective view of a tissue removal device having a cutting surface that is positioned within and in a coaxial relationship with the lumen of the device. The device includes a plurality of grasping members extending from the lumen.

In some embodiments, tissue removal device 10 comprises a tube, such as, for example, cannula 212, as shown in FIGS. 12-13. Cannula 212 may include a flexible character to facilitate manipulation during a surgical procedure.

However, in other embodiments, cannula 212 may be rigidly formed. The dimensions of the device, among other things, will depend on the site from which tissue must be removed. For example, the width of the epidural space is only about 3-5 mm for the thoracic region and about 5-7 mm for the lumbar region. Thus, the device, in various embodiments, can be designed for these specific areas.

Cannula 212 extends along a longitudinal axis and includes an opening 214. In some embodiments, opening 214 extends through the length of cannula 212 and terminates at tip 216. Tip 216 is at the distal end of cannula 212, and is configured to contact tissue, such as, for example, a ligamentum flavum. Tip 216 is in communication with opening 214. In some embodiments, cannula 212 can have one or more lumens. In various embodiments, the lumens or openings of cannula 212 may have alternate cross-sectional configurations. For example, the lumens may have a cross-sectional shape of oval, oblong, triangular, rectangular, square, polygonal, irregular, uniform, non-uniform, variable, tubular and/or tapered.

Cannula 212 is configured to provide suction at a surgical site. The suction eliminates the need to repeatedly retract device 10 from a surgical site during a surgical procedure. The suction is applied with sufficient force to pull a membrane or tissue, such as, for example, ligamentum flavum toward device 10. Tip 216 is configured to receive a portions of tissue and to retain tissue once a vacuum is created in opening 214. Thus, in various embodiments, tip 216 may be a blunt surface so as to prevent unintentional damage to tissue. In other embodiments, tip 216 is pointed to allow for easy pushing through tissues to reach a surgical site. The openings may be shaped as a regular or irregular polygon including arcuate, round, square, oblong, kidney shaped, crescent, or beveled shaped. In some embodiments, therapeutic agents can be delivered to the surgical site via the openings. In various embodiments, the tip of the cannula can be round or tapered.

In some embodiments, a cutting cannula 220 is sized to fit inside cannula 212. Cutting cannula 220 includes a distal cutting surface 222 configured to sever selected portions of tissue from a surgical site when brought into contact with tissue. Cutting cannula 220 may be axially movable within cannula 212, or may be fixedly attached to an inner surface of cannula 212 such that tip 216 and cutting surface 222 are spatially fixed with regard to one another. In some embodiments, cutting surface 222 is energized to cut through tissue. In various embodiments, an energy source is provided in communication with an edge of cutting surface 222 through a wire connected at the proximal end of flexible cutting surface 222 (not shown). The energy source may provide energy in the form of electrical, radiation, light, radiofrequency, ultrasound, cryotherapy, thermal, microwave or hydromechanical energy. In some embodiments, cannula 212 has a tip 216 that can be blunt and the cutting cannula 220 has a sharp cutting surface 222. In this way, unwanted tissue damage can be avoided as, for example, suction from cannula 212 can draw tissue into the cutting cannula 220 where the tissue in contact with this cutting cannula can be cut, while tissue that is not in contact with it will not be cut as it will contact a blunt surface. In some embodiments, the tip of the cannula can be curved at an angle from about 5 degrees to about 20 degrees or from about 10 degrees to about 30 degrees.

In some embodiments, cannula 212 includes one or more vents 226 along an outer surface, as shown in FIG. 12. Vents 226 provide a pressure valve when tip 216 of cannula 212 and/or cutting surface 222 of cutting cannula 220 are brought into contact with tissue L. Vents 226 allow for continuous suction of a surgical area even when tissue L blocks tip 216. In some embodiments, grasping members 30 are deployed to secure tissue and bring it into contact with cutting surface 222.

Figure 14:
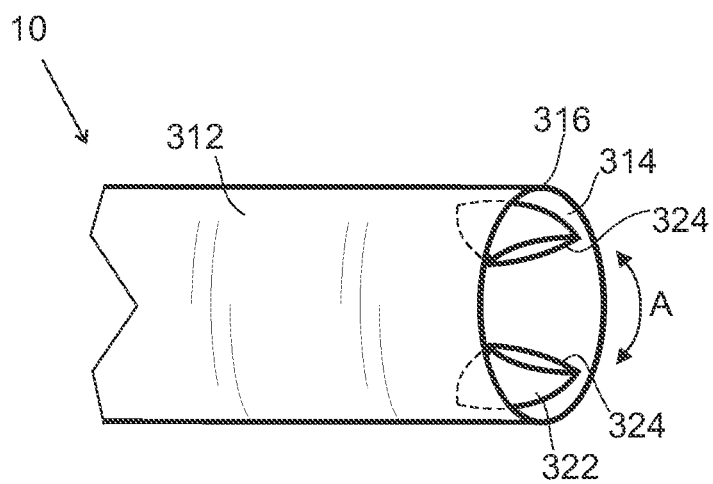
FIG. 14 illustrates a perspective view of a tissue removal device having a cutting surface in the form of a beak-shaped clamp inside the lumen such that when brought into contact with tissue, the clamp closes to cut and the tissue is removed by suction from a target site.

In some embodiments, as shown in FIG. 14 cannula 312 includes a beak-shaped cutter 322 embedded in opening 314. Beak-shaped cutter is disposed toward a distal end of lumen 312 such that beak-shaped cutter 322 extends slightly beyond tip 316. Cutter 322 is movable along the direction indicated by arrow A between a first configuration, such as, for example, an open state, and a second configuration, such as, for example, a cutting state. In some embodiments, cutter 322 is in communication with an actuator (not shown) to move between the deployed and retracted states. Cutter 322 includes cutting edges 324 configured to cut tissue when moved from the open state to the cutting state.

In some embodiments, a lubricant is provided to assist in the insertion of the device within the nerve and/or soft tissue. In some embodiments, the lubricant can be, without limitation, polyethylene glycol (PEG), hyaluronic acid, hyaluronan, lubricin, polyethylene glycol, and any combinations thereof.

In various embodiments, the device is coated with an antimicrobial coating and/or agents at discrete regions particularly at the cutting surface. The antimicrobial coating can include, for example, antibiotics, antifungal, antiviral agents or the like. Antimicrobial agents to treat infection include, by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In some embodiments, the device can be coated with an antiviral agent. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

In various embodiments, the tip of device 10 comprises a telescopic configuration. The tips can be manually or electronically movable so as to place the tips into a particular position within a surgical site. In certain embodiments, all or some of the tips comprise a telescopic configuration. In some embodiments, the tip is a navigational tool used to guide device 10 into a surgical site.

In some embodiments, the tips of device 10 each comprise indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the nerve and/or tissue.

In certain embodiments, device 10 may include switches for manually controlling the operation of device 10 by a medical practitioner. The switches can provide functions such as on/off, cooling, actuating grasping members or cutting surfaces, and/or predetermined cycles of heating and cooling by selectively and controllably communicating device 10 with an external material container.

In some embodiments, different monitors of temperature, gas pressure and location on device 10 can be attached to device 10. In some embodiments, thermal sensors may be used for measuring the temperature of the material and/or the tips. In some embodiments, device 10 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In some embodiments, device 10 is attached to a pressure source that is configured to supply the pressurized material described above. In some embodiments, without limitation, the pressure source can be a pump, a cannula and or a catheter.

With further reference to FIGS. 1-14, not shown is an overall glass or other insulating layer covering most of the structure. In some embodiments, the coating or insulating layer can be a polymer, glass or ceramic having a thickness from about 0.005 to about 0.5 mm thick or from about 0.01 to about 0.2 mm thick. The glass type insulation is typically applied by a conventional process of dipping each relevant component prior to assembly in liquid (molten) glass and then annealing the glass. In some embodiments, the coating or insulation layer does not cover the entire cannula. In some embodiments, the coating or insulation layer does cover the entire device.

In various embodiments, the device may include radiographic markers to help indicate position on imaging procedures (e.g., CT scan, X-ray, fluoroscopy, PET scan, etc.). These may be disposed on or a portion of the device and include, but are not limited to, barium, calcium phosphate, and/or metal beads.

In some embodiments, the cannula tip can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tip and can be closed when device 10 is inactive as device 10 is inserted towards the desired location. Once the nerve or soft tissue to cut is reached, grooves open, the material becomes activated to cut tissue L protruding into each groove as device 10 is manually pushed into it.

In certain embodiments, device 10 can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the internal passage of the sleeve and can run parallel to the internal passage such that the device can ablate and deliver a therapeutic material or barrier (e.g., polymer, cement, gel, etc.) to the area after ablating it.

Methods for Ablation

The present disclosure also provides methods for cutting and/or removing soft tissue while minimizing damage to adjacent nerve tissue. In assembly, operation and use, use of tissue removal device 10 is employed with a surgical procedure for treatment of localized pain affecting a section of a spine of a patient, as discussed herein. In use, to treat the affected tissue L, such as, for example, a ligamentum flavum or a frayed meniscus, a medical practitioner obtains access to a surgical site in any appropriate manner, such as through incision and retraction of tissues. It is envisioned that device 10 may be used in any existing surgical method or technique including open surgery, mini-open surgery, minimally invasive surgery, and percutaneous surgical implantation, whereby tissue is accessed through a micro-incision. Once access to the surgical site is obtained, the particular surgical procedure is performed for treating the spinal disorder In one some embodiments, the methods comprise disposing a tissue removal device 10 at a surgical site. Suction is applied through opening 14 while tip 16 is brought into contact with tissue L. The suction provides a gripping force to secure and stabilize a portion of tissue L to prepare it to be cut and removed. A portion of tissue L is suctioned beyond tip 16 partially into opening 14. In one embodiment, flexible cutting line 22 is movable between a first configuration, such as, for example, an implantation position, and a second configuration, such as, for example, a cutting position. While in the implantation position, flexible cutting line 22 is wrapped around an outer surface of cannula 12 at a point proximal to tip 16 so as to keep cutting loop 24 out of contact with tissue L. While in the cutting position, flexible cutting line 22 is positioned distally to tip 16 adjacent to tissue secured in opening 14. To cut tissue, flexible cutting line 22 is moved axially along a proximal direction through lumen 18 to reduce the size of cutting loop 24. As cutting loop 24 becomes smaller, flexible cutting line 22 cinches tissue L adjacent tip 16 to sever and remove a portion of tissue L, as discussed herein. Suction is continuously applied through opening 14 to remove the severed portion of tissue L through opening 14.

Alternatively or in addition to the use of suction as delineated above, grasping members 30 may be used to grasp and stabilize tissue L. In various embodiments, grasping members are movable between a first configuration, such as, for example, a retracted state, and a second configuration, such as, for example, a deployed state. As shown in FIG. 9, when in the deployed state grasping members 30 extend distally from tip 16 to contact and engage tissue L. As shown in FIG. 10, when in the retracted state grasping members 30 are close to tip 16 to facilitate implantation to a surgical site. A medical practitioner may manually move or use an actuator to move grasping members 30 from the retracted state to the deployed state to secure tissue L. Once secured, grasping members 30 are moved back to the retracted state to expose a portion of tissue L to be cut with flexible cutting line 22. In some embodiments, once tissue L is secured, a hook 40 is moved axially through opening 14 to cut through tissue L.

In some embodiments, the methods comprise disposing a tissue removal device 10 comprising cannula 112 at a surgical site. Suction is applied through lumen 114 while tip 116 is brought into contact with tissue L. The suction provides a gripping force to secure and stabilize a portion of tissue L to prepare it to be cut and removed. A portion of tissue L is suctioned beyond tip 116 partially into lumen 114. A cutting line 122, similar to flexible cutting line 22, is advanced to the surgical site adjacent to cannula 122. Cutting loop 124 is applied to tissue L to cut and separate tissue.

In various embodiments, the inner tube is hollow and insulated and comprises an opening at a distal end, and the hollow tube comprises a nonconductive material comprising plastic, glass, ceramic, porcelain, composite polymers and rubber.

In other embodiments, the methods of the present disclosure further include delivering cement and/or a polymer through a small channel, for injection at the site of the nerve and/or soft tissue resection to provide a physical barrier at the location of the nerve resection to prevent temporary or permanent nerve regrowth, repair and return of the pain symptoms.

The barrier material utilized can be any suitable material effective to prevent or at least substantially inhibit the migration of substances that regrow tissue. Illustratively the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the device to a source of navigational capability to allow easier pushing through the tissues. In various embodiments, the methods of ablation disclosed herein can include a pre-procedure step wherein the device can be coupled to a CT or MRI machine so that the target nerve and/or soft tissue to be ablated can be identified and accurately located during the resection procedure.

In various embodiments, kits are provided that include device 10. The kits can include at least one cannula and at cutting line. In some embodiments, the cannula and cutting line is made reusable for multiple procedures after cleaning and sterilization.

Specific clinical application of this instrument include resection of nerves causing facet and discogenic back and leg pain, resection of soft tissue causing stenosis pain symptoms, and many other orthopedic and oral maxillofacial pain. Many other painful conditions associated with arthroscopic, otolaryngological or spinal procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A medical device for a minimally invasive surgical procedure comprising a cannula having an opening at a distal tip of the cannula, the opening configured for suction of a surgical site, and a movable tissue capture member extending from a single distal opening of a lumen such that only the movable tissue capture member extends from the lumen, the lumen disposed adjacent to and parallel to a longitudinal axis of the cannula, the lumen also being disposed non-coaxially to the cannula, the movable tissue capture member having a portion disposed adjacent to the cannula, the movable tissue capture member configured to capture tissue when moved in a first position, wherein the movable tissue capture member is flexible and comprises a stem portion and a cutting line in the form of a loop, the loop comprising a sharp area for cutting the tissue, and when in an undeployed position, the cutting line is wrapped around an outer surface of the cannula at a point adjacent to the distal tip, wherein the opening terminates at the distal tip and the movable tissue capture member extends from the distal tip.

2. The medical device of claim 1, wherein the distal tip of the cannula is blunt, the lumen having a length that is less than a length of the cannula and the movable capture member is disposed within the lumen; and the movable capture member extends distally from the opening of the cannula when in the first position to contact the tissue.

3. The medical device of claim 2, wherein the movable tissue capture member is configured to contact the tissue when in the first position and cut the tissue when in a second position.

4. The medical device of claim 2, wherein the cannula has a larger diameter relative to a diameter of the lumen.

5. A medical device of claim 1, wherein the loop is rigid and comprises a blunt area to prevent tissue damage.

6. A medical device of claim 5, wherein the blunt area is coated with a polymer to prevent the tissue damage.

7. A medical device of claim 6, wherein the sharp area includes an electrosurgical lead or a sharpened surface.

8. The medical device of claim 1, wherein the movable tissue capture member comprises shape memory material.

9. A medical device for a minimally invasive surgical procedure comprising a cannula having an opening at a distal tip of the cannula, the opening configured for suction of a surgical site, and a movable tissue capture member extending from a single distal opening of a lumen such that only the movable tissue capture member extends from the lumen, the lumen disposed adjacent to and parallel to a longitudinal axis of the cannula, the lumen also being disposed non-coaxially to the cannula, the movable tissue capture member having a cutting surface and configured to capture tissue when moved in a first position, wherein the movable tissue capture member is flexible and comprises a stem portion and a cutting line in the form of a loop, the loop comprising a sharp area for cutting the tissue, and when in an undeployed position, the cutting line is wrapped around an outer surface of the cannula at a point adjacent to the distal tip, wherein the opening terminates at the distal tip and the movable tissue capture member extends from the distal tip.

10. The medical device of claim 9, wherein the cutting surface includes an electrosurgical lead or a sharpened surface.

11. The medical device of claim 9, wherein the movable tissue capture member comprises shape memory material.

12. The medical device of claim 9, wherein the cannula comprises at least one vent configured to facilitate suction of the surgical site.

* * * * *